(12) United States Patent
Chheda et al.

(10) Patent No.: US 10,501,430 B2
(45) Date of Patent: Dec. 10, 2019

(54) PROCESS FOR THE RECOVERY OF FURFURAL

(71) Applicant: SHELL OIL COMPANY, Houston, TX (US)

(72) Inventors: Juben Nemchand Chheda, Houston, TX (US); Jean Paul Andre Marie Joseph Ghislain Lange, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 16/346,317

(22) PCT Filed: Oct. 30, 2017

(86) PCT No.: PCT/US2017/058951
§ 371 (c)(1),
(2) Date: Apr. 30, 2019

(87) PCT Pub. No.: WO2018/085182
PCT Pub. Date: May 11, 2018

(65) Prior Publication Data
US 2019/0276422 A1 Sep. 12, 2019

Related U.S. Application Data

(60) Provisional application No. 62/415,533, filed on Nov. 1, 2016.

(51) Int. Cl.
*C07D 307/50* (2006.01)
*B01D 3/36* (2006.01)

(52) U.S. Cl.
CPC ............. *C07D 307/50* (2013.01); *B01D 3/36* (2013.01)

(58) Field of Classification Search
CPC .................................. C07D 307/50; B01D 3/36
See application file for complete search history.

(56) References Cited

U.S. PATENT DOCUMENTS

| | | | |
|---|---|---|---|
| 2,078,241 A | 4/1937 | Fulmer et al. | |
| 2,536,732 A | 1/1951 | Dunlop | |
| 3,549,319 A | 12/1970 | Wilson et al. | |
| 4,409,032 A | 10/1983 | Paszner et al. | |
| 4,461,648 A | 7/1984 | Foody | |
| 4,533,743 A | 8/1985 | Medeiros et al. | |
| 5,536,325 A | 7/1996 | Brink | |
| 5,789,210 A | 8/1998 | Ho et al. | |
| 5,820,687 A | 10/1998 | Farone et al. | |
| 6,475,768 B1 | 11/2002 | Otero et al. | |
| 7,741,084 B2 | 6/2010 | Viitanen et al. | |
| 7,741,119 B2 | 6/2010 | Viitanen et al. | |
| 7,781,191 B2 | 8/2010 | Dunson, Jr. et al. | |
| 8,168,807 B2 | 5/2012 | Wabnitz et al. | |
| 8,466,242 B2 | 6/2013 | Geremia et al. | |
| 2003/0162271 A1 | 8/2003 | Zhang et al. | |
| 2009/0061490 A1 | 3/2009 | Edwards et al. | |
| 2010/0019191 A1 | 1/2010 | Hoffer et al. | |
| 2010/0312028 A1 | 12/2010 | Olson et al. | |
| 2012/0107887 A1 | 5/2012 | Chheda et al. | |
| 2012/0122152 A1 | 5/2012 | Blackbourn et al. | |
| 2012/0157697 A1 | 6/2012 | Burket et al. | |
| 2012/0302765 A1 | 11/2012 | Dumesic et al. | |
| 2013/0232854 A1* | 9/2013 | Haan ................. | B01D 11/0426 44/307 |
| 2013/0295629 A1 | 11/2013 | Weider et al. | |
| 2014/0018555 A1 | 1/2014 | De Vries et al. | |
| 2014/0107355 A1 | 4/2014 | Dumesic et al. | |

FOREIGN PATENT DOCUMENTS

| | | |
|---|---|---|
| EP | 1727890 A1 | 12/2006 |
| EP | 1863901 A1 | 12/2007 |
| SU | 1365674 A1 | 7/1996 |
| WO | 9742307 A1 | 11/1997 |
| WO | 2007009463 A2 | 1/2007 |
| WO | 2007028811 A1 | 3/2007 |
| WO | 2007136762 A2 | 11/2007 |
| WO | 2008119082 A2 | 10/2008 |
| WO | 2009109631 A1 | 9/2009 |
| WO | 2009130386 A1 | 10/2009 |
| WO | 2011161141 A1 | 12/2011 |
| WO | 2012027279 A1 | 3/2012 |
| WO | 2012041990 A1 | 4/2012 |
| WO | 2014105289 A1 | 7/2014 |
| WO | 2016025678 A1 | 2/2016 |
| WO | 2016025679 A1 | 2/2016 |

OTHER PUBLICATIONS

International Search Report and Written Opinion received for PCT Patent Application No. PCT/US2017/058951, dated Jan. 2, 2018, 8 pages.
International Search Report and Written Opinion received for PCT Patent Application No. PCT/US2015/044994, dated Nov. 2, 2015, 8 pages.
International Search Report and Written Opinion received for PCT Patent Application No. PCT/US2015/044990, dated Nov. 2, 2015, 7 pages.
International Search Report and Written Opinion received for PCT Patent Application No. PCT/US2017/058942, dated Jan. 19, 2018, 9 pages.
International Search Report and Written Opinion received for PCT Patent Application No. PCT/US2017/058936, dated Feb. 7, 2018, 9 pages.

(Continued)

*Primary Examiner* — Timothy R Rozof

(57) ABSTRACT

Disclosed is a process for the extraction of furfural including: (a) subjecting a composition comprising furfural, water, at least one inorganic acid, at least one organic acid and a solvent mixture comprising an aromatic solvent and an oxygenate solvent, to a first separation step providing: (i) a first organic phase; (b) subjecting the first organic phase to a first distillation step providing: (i) a first top stream comprising furfural and a portion of the at least one organic acid; (c) subjecting the first top stream from step (b) to a second separation step providing: (i) a second top stream enriched with furfural; (d) subjecting the second top stream from step (c) to a second distillation step providing: (i) a third top stream comprising a furfural-water azeotrope, and (ii) a third bottom stream comprising furfural.

10 Claims, 1 Drawing Sheet

(56) References Cited

OTHER PUBLICATIONS

International Search Report and Written Opinion received for PCT Patent Application No. PCT/US2017/058939, dated Dec. 14, 2017, 8 pages.
Brown et al., "Fast Pyrolysis and Bio-Oil Upgrading", Biomass-to-Diesel Workshop; Pacific Northwest National Laboratory, Sep. 5-6, 2006.
Zeitsch"The Chemistry and Technology of Furfural and its Many By-Products", Sugar Series, vol. 13, Feb. 1, 2000, pp. 48-51 and 303-306.
Galbe et al., "A Review of the Production of Ethanol from Softwood", Applied Microbiology and Biotechnology, vol. 69, 2002, pp. 618-628.
Ong, "Conversion of Lignocellulosic Biomass to Fuel Ethanol—A Brief Review", The Planter, vol. 80, Issue No. 941, Aug. 2004, pp. 517-524.
Moller, "Cell Wall Saccharification", Outputs from the EPOBIO Project, Nov. 2006, pp. 1-69.
Mosier et al., "Features of Promising Technologies for Pretreatment of Lignocellulosic Biomass", Bioresource Technology, vol. 96, 2005, pp. 673-686.
Holtzapple et al., "The Ammonia Freeze Explosion (AFEX) process—A Practical Lignocellulose Pretreatment", Applied Biochemistry and Biotechnology, vol. 28/29, Issue No. 1, Mar. 1991, pp. 59-74.
Kumar et al., "Methods for Pretreatment of Lignocellulosic Biomass for Efficient Hydrolysis and Biofuel Production", Industrial & Engineering Chemistry Research, vol. 48, Issue No. 8, 2009, pp. 3713-3729.
Lavarack et al., "The Acid Hydrolysis of Sugarcane Bagasse Hemicellulose to Produce Xylose, Arabinose, Glucose and other Products", Biomass & Bioenergy, vol. 23, Issue No. 5, 2002, pp. 367-380.
Yang et al., "One-Step Catalytic Transformation of Carbohydrates and Cellulosic Biomass to 2, 5 Dimethyltetrahydrofuran for Liquid Fuels", Chem Sus Chem, vol. 3, Issue No. 5, May 25, 2010, pp. 597-603.
Lange et al., "Furfural-A Promising Platform for Lignocellulosic Biofuels", Chem Sus Chem, vol. 5, Issue No. 1, Jan. 9, 2012, pp. 150-166.
Nhien et al., "Design and Optimization of Intensified Biorefinery Process for Furfural Production Through a Systematic Procedure", Biochemical Engineering Journal, vol. 116, Apr. 5, 2016, pp. 166-175, XP029805891.
International Search Report and Written Opinion received for PCT Patent Application No. PCT/US2015/044981, dated Nov. 2, 2015, 8 pages.

\* cited by examiner

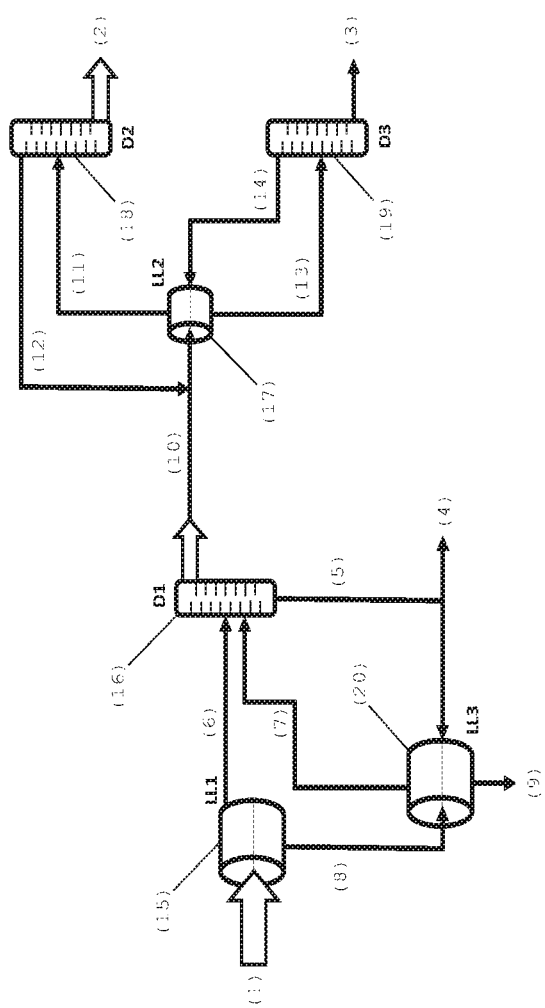

PROCESS FOR THE RECOVERY OF FURFURAL

CROSS REFERENCE TO RELATED APPLICATIONS

This is a national stage application of International Application No. PCT/US2017/058951, filed 30 Oct. 2017, which claims benefit of priority to U.S. Provisional Patent Application No. 62/415,533, filed 1 Nov. 2016.

FIELD OF THE INVENTION

The present invention relates to a process for the high recovery/extraction of furfural from a composition in an energy efficient manner.

BACKGROUND OF THE INVENTION

Furfural is a useful precursor for industrial chemicals, in particular to produce furan and its derivatives.

Furfural may be produced from the hydrolysis of feedstock comprising lignocellulosic biomass. Lignocellulosic biomass comprises mainly hemicelluloses and cellulose, and smaller portions of lignin and protein. Hemicelluloses are a branched polysaccharide of heterogeneous monosaccharide content. Their molecular structure includes the five-carbon monosaccharides ('pentose(s)') xylose and arabinose, as well as the six-carbon monosaccharides ('hexose(s)') mannose, galactose and rhamnose. Due to their xylose and arabinose content, hemicelluloses are a suitable source of monomeric and polymeric pentoses. In comparison, cellulose is a linear-polysaccharide made up of polymerised glucose (a six-carbon monosaccharide/hexose). Compared to cellulose, hemicelluloses are easier to breakdown into their constituent monosaccharides.

Commercially available feedstock comprising lignocellulosic biomass includes bagasse, which is the fibrous matter that remains after sugarcane or sorghum stalks are crushed their juices extracted. An established continuous process for the production of furfural from bagasse is the Rosenlew process, the details of which are discussed in "The Chemistry and Technology of Furfural and its Many By-Products", 1st Edition, K. Zeitsch, pages 48-51 and 303-306.

WO2012041990 describes the production of furfural from bagasse-derived hemicellulose, via its gaseous acid catalysed hydrolysis to pentoses, which are then dehydrated to produce furfural.

WO2016025678 describes the production of furfural, where initially hemicellulose is hydrolysed in a solution comprising α-hydroxysulfonic acid, a portion of the α-hydroxysulfonic acid is then removed from the hydrolysis reaction product to produce an acid-removed stream, and finally the acid-removed stream is subjected to a dehydrating step to produce furfural.

WO2016025679 describes a hydrolysis step, which is buffered to, preferably, less than pH 1, followed by a dehydrating step to produce furfural.

In both WO2016025678 and WO2016025679, during the dehydration reaction step, a "bi-phasic" dehydration reaction mixture is formed by the addition of 'a water-immiscible organic phase' (i.e. a solvent) into the dehydration reaction mixture. The dehydration reaction mixture is then separated into an aqueous product stream, and an organic product stream comprising a portion of furfural. However, WO2016025678 and WO2016025679 do not disclose how furfural can be fully recovered and purified from the organic product stream comprising furfural. Further, WO2016025678 and WO2016025679 do not disclose how furfural remaining in the aqueous product stream can be efficiently recovered and purified from the aqueous product stream.

Solvent extraction of furfural from an aqueous environment is complicated by the carry-over of water into the organic phase, as well as the formation of a furfural-water azeotrope. The extent of the water carry-over depends on the solvent used. Oxygenate solvents, such as those of phenolic compounds, carry more water into the organic phase (approximately around 10,000 ppm to around 40,000 ppm), as compared to aromatic solvents (approximately around 200 ppm to around 1,000 ppm). Further, in an aqueous environment, furfural can form a furfural-water azeotrope can be formed. It is known in the art of extracting chemical compounds from mixtures of compounds that the presence of any azeotrope increases the energy consumption of a given process, as well as complicating the step and the equipment needed for that process.

Aromatic solvents have a lesser tendency to carry-over water and therefore are less likely to favour the formation of a furfural-water azeotrope, so on the face of it, aromatic solvents seem good candidates for the extraction furfural; however due to furfural's properties, aromatic solvents' ability to extract furfural is lower than that of oxygenate solvents, which potentially decreases the overall furfural recovery when aromatic solvents are used.

Process for the production of furfural from biomass leads to the formation of humins and tar, which can adversely interfere with the extraction and purification of furfural. Humins are dark, amorphous and undesirable acid by-products and resinous material resulting from sugars, and other organic compound degradation. Tar is a generic reference to organic material which is insoluble in water, which is dark in colour, and which tends to become viscous and very dark to almost black when concentrated. Particularly, the separation of an organic phase from an aqueous phase, and/or the later separation or purification steps can be adversely affected by humins and tar.

The inventors of the present invention have observed that such problems are applicable in the formation, and during the extraction and purification of furfural from lignocellulosic biomass, but may be alleviated by the use of oxygenate solvents, rather than aromatic solvents.

Regarding energy consumption, the Rosenlew process uses azeotropic distillation to isolate furfural from the reaction mix by, and does not use solvent extraction. The Rosenlew process consumes about 10 tonnes of steam to recover each tonne of furfural.

It would, therefore, be advantageous to provide a process for the recovery of furfural that is more energy-efficient, which provides a high-yield of furfural than the prior art processes, as well as one which does not suffer from the interference of humins and tar.

SUMMARY OF THE INVENTION

Accordingly, the present invention provides a process for the extraction of furfural from a composition comprising furfural, water, at least one inorganic acid, at least one organic acid and a solvent mixture comprising an aromatic solvent and an oxygenate solvent wherein each of the solvents in the solvent mixture has a boiling point higher than of furfural, said process comprising: (a) subjecting the composition to a first liquid-liquid separation step to provide: (i) a first organic phase comprising the solvent mixture, a portion of the furfural and a portion of the at least one organic acid, and (ii) a first aqueous phase comprising the remainder of the furfural, and the remainder of the at least one organic acid; (b) subjecting the first organic phase to a first distillation step to provide: (i) a first top stream comprising furfural and a portion of the at least one organic acid, and (ii) a first bottom stream comprising the solvent mixture; (c) subjecting the first top stream from step (b) to a second liquid-liquid separation step to provide: (i) a second top stream enriched with furfural and a portion of the at least one organic acid, and (ii) a second bottom stream comprising the remainder of the furfural and a portion of the at least one organic acid; (d) subjecting the second top stream from step (c) to a second distillation step to provide: (i) a third top stream comprising a furfural-water azeotrope and a portion of the at least one organic acid, and (ii) a third bottom stream comprising furfural.

BRIEF DESCRIPTION OF THE DRAWING

FIG. 1 shows a simplified schematic diagram of an embodiment of the process according to the invention.

DETAILED DESCRIPTION OF THE INVENTION

The present inventors have surprisingly found that the process for the extraction of furfural according to the present invention provides a higher yield of furfural than known processes, and consumes less energy to produce each tonne of furfural, suitably, by consuming less than 6 tonnes of steam to recover each tonne furfural with a furfural recovery of around 99%.

In the process according to the present invention, furfural is extracted from a composition comprising furfural, water, at least one organic acid and a solvent mixture comprising an aromatic solvent and an oxygenate solvent wherein each of the solvents in the solvent mixture has a boiling point higher than of furfural.

In an embodiment of the present invention the composition may be derived from a product stream of a pentose dehydration step, wherein a pentose feed stream is dehydrated.

Suitably, the pentose dehydration step dehydrates a pentose feed stream comprising monomeric and polymeric pentoses, which is derived from a hydrolysis step wherein a lignocellulosic biomass is hydrolysed in the presence of at least one inorganic acid; although as an alternative, other processes may also be used to hydrolyse the lignocellulosic biomass, such as ones which may use basic or neutral pH conditions. Suitably, the lignocellulosic biomass hydrolysis step is as described in WO2016025678 and WO2016025679.

Where used for the hydrolysis of lignocellulosic biomass, suitably, the at least one inorganic acid may be selected from, such as but not limited to, hydrochloric acid, nitric acid, phosphoric acid, boric acid sulphuric acid and α-hydroxysulfonic acid, or combinations thereof.

Suitably, some types of lignocellulosic biomass may intrinsically contain at least one organic acid, or will form at least one organic acid upon being subjected to the hydrolysis. Examples of such acids include, but are not limited to, formic acid, acetic acid, lactic acid, glycolic acid, levulinic acid, oxalic acid and citric acid, or combinations thereof. When using such types of biomass material, the need to add at least one acid inorganic acid may be reduced or even eliminated as the in-situ generated acid may provide the necessary acidic pH.

According to an embodiment of the invention, the composition may be derived from the product stream of a pentose dehydration step; said product stream is also hereinafter referred to as the "dehydration product stream".

Suitably, the pentose dehydration step takes place in a dehydration reaction mixture, where the dehydration of monomeric and polymeric pentoses is catalysed by at least one inorganic acid at an elevated temperature, although at least one organic acid may also take part in such catalysis.

The dehydration reaction mixture comprises the pentose feed stream, at least one inorganic acid, at least one organic acid and furfural; the level of the furfural depending on how long the pentose dehydration step has been running.

The at least one inorganic acid and the at least one organic acid present in the dehydration reaction mixture will have carried through in the pentose feed stream from the hydrolysis step to the pentose dehydration step, where the hydrolysis step precedes the pentose dehydration step. However, if the hydrolysis step was carried out under basic or neutral pH conditions as an alternative, or if it is determined that the pH of the dehydration reaction mixture is not acidic enough, more inorganic acid may be added to the dehydration reaction mixture.

Preferably, the pentose dehydration step is carried out at the elevated temperature of at least 100° C., more preferably at least 110° C., and even more preferably at least 140° C. Preferably, the pentose dehydration step is carried out at the elevated temperature of at most 250° C., more preferably at most 200° C., and even more preferably at most 150° C.

Preferably, the pentose dehydration step is carried out for a period of at least 1 second, more preferably at least 5 minutes, even more preferably at least 10 minutes and most preferably at least 30 minutes. Preferably, the pentose dehydration step is carried out for a period of at most 24 hours, more preferably at most 12 hours, even more preferably at most 5 hours and most preferably at most 2 hours.

A solvent mixture comprising an aromatic solvent and an oxygenate solvent, wherein each of the solvents in the solvent mixture has a boiling point higher than of furfural, may be added to the dehydration reaction mixture. The presence of the solvent mixture in the dehydration reaction mixture creates an aqueous phase and an organic phase.

Preferably, the dehydration reaction mixture to solvent mixture ratio is at least 1 to 0.05% vol., more preferably said ratio is 1 to 0.1% vol., even more preferably said ratio is 1 to 0.25% vol., most preferably said ratio is 1 to 0.4% vol.

Preferably, the dehydration reaction mixture to oxygenate solvent ratio is at most 1 to 2.5% vol., more preferably said ratio is 1 to 1.25% vol., even more preferably said ratio is 1 to 0.75% vol., most preferably said ratio is 1 to 0.6% vol.

Preferably, the aromatic solvent is selected from compounds such as, but not limited to, 1-ethyl-2,3-dimethylbenzene, 1-ethyl-2,5-dimethylbenzene, 1-ethyl-2,4-dimethylbenzene, 1-ethyl-3,4-dimethylbenzene, 1,2,3,5-tetramethylbenzene, 1,2,3,4-tetramethylbenzene, 1,2,4,5-tetramethylbenzene, naphthalene, 1-methylnaphthalene, 2-methylnaphthalene, n- and sec-propyl-methyl benzenes (with the methyl group located in 2, 3, 4 or 5 position) n- and sec-butyl benzene and n- and sec-pentyl benzene. Suitably, the aromatic solvent may be a mixture of any combination thereof.

Preferably, the oxygenate solvent is selected from the group consisting of, but not limited to, propyl guaiacol, propyl syringol, guaiacyl propanol, syringyl propanol, nonyl phenol, o-, m-, p-substituted cresols, guaiacol, 2-methoxy-4-propylphenol, eugenol, sec-butyl phenol and 2,6-xylenol, 2,5-xylenol. Optionally, tetrahydrofuranic compounds may also be selected. Suitably, the oxygenate solvent may be a mixture of any combination thereof.

The solvent mixture may be added to the dehydration reaction mixture at the start of, or part way through, the pentose dehydration step. Suitably, the solvent mixture may also be added to the dehydration product stream to form the composition, if the pentose dehydration step did not occur in the presence of the solvent mixture.

However, preferably, the solvent mixture may be added to the dehydration reaction mixture at the start of the pentose dehydration step. Optionally, the source of the solvent mixture may be a recycle stream from one or more of steps of the process of the present invention, such stream being recycled as a feed to the pentose dehydration step.

In one embodiment of the process, only the aromatic solvent may be added to the dehydration reaction mixture at the start of, or part way through, the pentose dehydration step, and the oxygenate solvent being added at the of end the pentose dehydration step.

Preferably, in another embodiment of the process, only the oxygenate solvent may be added to the dehydration reaction mixture at the start of, or part way through, the pentose dehydration step, and the aromatic solvent being added at the of end the pentose dehydration step.

When the solvent mixture is present in the dehydration reaction mixture, the formation of furfural mainly takes place in the aqueous phase. Therefore the amount of furfural in the organic phase varies depending on how far the pentose dehydration step has progressed.

Suitably, both the aromatic solvent and oxygenate solvent has selectivity towards furfural over water and over the at least one inorganic acid, however their selectivity over the at least one organic acid differ.

The difference in selectivity over the at least one organic acid between the aromatic solvent and oxygenate solvent differ due the different extent to which each type of solvent carry-over water into the organic phase. Oxygenate solvents, such as those of phenolic compounds, carry more water into the organic phase (approximately around 10,000 ppm to around 40,000 ppm), as compared to aromatic solvents (approximately around 200 ppm to around 1,000 ppm). Such water carry-over facilitates the partitioning of the at least one organic acid into the organic phase. Ultimately the at least one organic acid needs to be removed from the furfural product of the process.

While the partitioning of the at least one organic acid into the organic phase is undesirable, the difference in water carry-over into the organic phase has the advantage that more furfural may be extracted into the organic phase. Due to the intrinsic properties of furfural, solvents that are substantially immiscible in water have varying ability to extract furfural into an organic phase. Without being bound to a particular theory, this may be linked to the extent of water carry-over into the organic phase, such that oxygenate solvents have a higher furfural extraction capacity than aromatic solvents.

A further advantage observed by the inventor of the present process is that the extent of humin precipitation and the adverse effects of tar formation vary according to whether an organic or an oxygenate solvent is present in the dehydration reaction mixture or the composition. Such issues are less of a problem with oxygenate solvents that with aromatic solvents, probably again due to the extent of their respective water carry-over.

Therefore the inventor of the present process have found that a solvent mixture comprising an aromatic solvent and an oxygenate solvent surprisingly overcomes said unfavourable effect of each other.

However, also due to the extent of water carry-over into the organic phase of an oxygenate solvent, furfural in the organic phase tends to form a furfural-water azeotrope, complicating the removal of furfural from the composition and making it more energy demanding.

The inventor of the present process have surprisingly found that only the organic phase derived from the composition has to be processed to recover furfural, and therefore any increase in energy cost of processing furfural-water azeotrope, and the removal of an at least one organic acid, is offset by not needing to process an aqueous phase, as processing the latter involves boiling off large quantities of water.

FIG. 1 shows a simplified schematic diagram of an embodiment of process according to the invention, illustrating that a composition (1) is supplied to a first liquid-liquid separator (15), which provides a first organic phase (6) comprising the oxygenate solvent and a portion of the furfural, which is conveyed to the first distillation column (16).

In the process according to the present invention, furfural is extracted from a composition (1) comprising furfural, water, at least one organic acid and a solvent mixture comprising an aromatic solvent and an oxygenate solvent wherein each of the solvents in the solvent mixture has a boiling point higher than of furfural.

To commence the extraction of furfural from the composition, the composition is subjected to a first liquid-liquid separation step in a first liquid-liquid separator (15) to provide: (i) a first organic phase (6) comprising the solvent mixture, a portion of the furfural and a portion of the at least one organic acid, and (ii) a first aqueous phase (8) comprising the remainder of the furfural and the remainder of the at least one organic acid.

Preferably, the first liquid-liquid separation may be operated at a temperature of at most 200° C., more preferably at a temperature of at most 180° C., even more preferably at a temperature of at most 160° C., even more preferably at a temperature of at most 150° C., so long as the liquid separates into two phases at the separation temperature.

Preferably, the first liquid-liquid separation may be operated at a temperature of at least ambient temperature, more preferably at a temperature of at least 60° C., even more preferably at a temperature of at least 100° C., even more preferably at a temperature of at least 130° C., so long as the liquid separates into two phases at the separation temperature.

The first liquid-liquid separation step is carried out in any suitable liquid-liquid separator as would be known to the person skilled in the art.

Prior to undergoing the first liquid-liquid separation step, the composition may optionally be routed through, preferably, a solid/liquid separation step to remove any insoluble humins or other tar that may have been formed during the dehydration step.

In the process of the present invention the first organic phase (6) is subjected to a first distillation step to provide: (i) a first top stream (10) comprising furfural and a portion of the at least one organic acid, and (ii) a first bottom stream (5) comprising the solvent mixture.

Furfural has a boiling point at ambient pressure of about 161° C. and the furfural-water azeotrope has a boiling point at ambient pressure of about 98° C., and as the aromatic solvent and oxygenate solvent both have a boiling point higher than that of furfural and the furfural-water azeotrope, a first top stream comprising furfural is obtained. Suitably, the greater the difference between the boiling point of furfural and the oxygenate solvent, the easier and cleaner the separation between these compounds will be.

Suitably the aromatic solvent may be 1-methylnaphthalene, which has a boiling point of about 242° C. at ambient pressure, and suitably this gives sufficient difference in respective boiling points to achieve 100% furfural purity.

Suitably the oxygenate solvent may be sec-butyl phenol, which has a boiling point of around 240° C. at ambient pressure, and suitably this gives sufficient difference in respective boiling points to achieve good furfural separation.

The presence of a portion of the at least one organic acid in the first top stream, as well as the tendency for furfural to form an azeotrope with water complicate the recovery of furfural.

To overcome this, the inventors of the present invention have introduced a second liquid-liquid separation step into the process of the present invention, which takes advantage the property of the furfural-water azeotrope to phase separate under certain temperatures.

The inventors of the present invention have suitably introduced an energy efficient process loop that not only assists to separate furfural from the furfural-water azeotrope, but also recycles any remaining furfural-water azeotrope back as a feed to the second liquid-liquid separator and thereby improving overall furfural recovery.

Therefore in the process of the present invention, the first top stream (10) from the first distillation step is subjected to a second liquid-liquid separation step (17) to provide: (i) a second top stream (11) enriched with furfural and a portion of the at least one organic acid, and (ii) a second bottom stream (13) comprising the remainder of the furfural and a portion of the at least one organic acid.

Preferably, the second liquid-liquid separation may be operated at a temperature of at most 120° C., more preferably at a temperature of at most 100° C., even more preferably at a temperature of at most 80° C., even more preferably at a temperature of at most 60° C., so long as the liquid separates into two phases at the separation temperature.

Preferably, the second liquid-liquid separation may be operated at a temperature of at least ambient temperature, more preferably at a temperature of at least 30° C., even more preferably at a temperature of at least 40° C., even more preferably at a temperature of at least 50° C., so long as the liquid separates into two phases at the separation temperature.

In the process of the present invention, following the second liquid-liquid separation step (17), the second top stream (11) from the second liquid-liquid separation step (which is enriched with furfural) is subjected to a second distillation step (18) to provide: (i) a third top stream (12) comprising a furfural-water azeotrope and a portion of the at least one organic acid, and (ii) a third bottom stream (2) comprising furfural.

To avoid energy loss through heat loss due to the introduction of new material to the process, as well as to increase the utility of the solvent mixture, process of the present invention the following steps may be carried out.

Optionally the solvent mixture is recycled such that the first aqueous phase (5) from the first liquid-liquid separation step (15) and a portion of the first bottom stream (5) from the first distillation step are conveyed to a third liquid-liquid separator (20) and subjected to a third liquid-liquid separation step to provide: (i) a fifth top stream (7) comprising furfural and the solvent mixture; and (ii) an aqueous waste stream (9) comprising water and at least one organic acid.

Optionally in the process of the present invention, the fifth top stream (14) is recycled to the first distillation step (16).

Optionally in the process of the present invention, the second bottom stream (13) of the second liquid-liquid separation step is subjected to a third distillation step (19) to provide: (i) a fourth top stream (14) comprising a furfural-water azeotrope and (ii) a fourth bottom stream (3) comprising water and a portion of the at least one organic acid, wherein said stream is recycled back to feed the second liquid-liquid separation step (17) of step (c).

Optionally in the process of the present invention, a portion of the first bottom stream (5) of the second distillation step is conveyed to the third liquid-liquid separator (20) and the portion is in the range of from 5% vol. to 80% vol. of the amount of the second bottom stream (4) exiting the first distillation column (16).

Optionally in the process of the present invention, a portion of the first bottom stream (5) of the second distillation step is conveyed to the third liquid-liquid separator (20) and the portion is 10% vol. of the amount of the second bottom stream (4) exiting the first distillation column (16).

Optionally, each of the first distillation step (16), the second distillation step (18) and the third distillation step (19) may be either atmospheric distillation, and vacuum distillation, where if the latter the vacuum column may be operated at a pressure down to around 0.00133 MPa (10 mmHg).

EXAMPLE

A process line up as depicted in FIG. 1 was assessed for furfural recovery using process modelling Aspen plus (Version 7.3) software licensed from Aspen Technology Inc., MA.

The modelled process line up is representative of a furfural separation scheme from a process stream containing furfural on a furfural manufacturing plant.

The results obtained in this example are representative of expected furfural recovery rates, fraction of furfural recovery from feed stream, furfural purity, heat duty (MW), and steam usage measured in tonne of steam/tonne of furfural produced.

Thermodynamic data contained in 'NRTL-HOC property method' set was used in this simulation.

Steam consumption in the process line up was determined on the basis of using 4.48 MPa high pressure steam.

The feed stream (1) contains water, furfural, acetic acid (as at least one organic acid), mixture of 1-methyl naphthalene (1-MNP) (representative of an aromatic solvent with a boiling point higher than that of furfural) and sec-butyl phenol (SBP) (representative of an oxygenate solvent with a boiling point higher than that of furfural) in 1:1 ratio on weight basis.

Separation scheme enables separation of furfural from the composition with high purity and allows for recycle of solvent for re-use in the process.

Table 1 present all the process stream data output.

Table 2 and 3 give process operating conditions and results summary for distillation columns and liquid-liquid separators used in the process line-up. Table 4 presents the summary of results for furfural separation scheme.

Based on the simulation output this separation process line up consumes about 4.3 tonne steam/tonne furfural produced. This is about 57% reduction in steam usage compared to consumption of 10 tonne steam/tonne furfural produced in the state-of-the-art Rosenlew's process for commercial furfural production.

TABLE 1

Stream Summary Results

| Stream # | 13 | 11 | 3 | 14 | 5 | 10 | 12 | 2 |
|---|---|---|---|---|---|---|---|---|
| Component Mass Flow | | | | | | | | |
| Water (tonnes/day) | 85.3 | 161.2 | 0.0 | 85.3 | 0.0 | 70.0 | 91.2 | 70.0 |
| Furfural (tonnes/day) | 693.1 | 27.1 | 624.0 | 69.1 | 0.8 | 624.0 | 27.1 | 0.0 |
| Acetic Acid (tonnes/day) | 47.1 | 13.2 | 1.6 | 45.6 | 0.0 | 13.0 | 1.7 | 11.4 |
| SBP (tonnes/day) | 0.0 | 0.0 | 0.0 | 0.0 | 3990.0 | 0.0 | 0.0 | 0.0 |
| 1-MNP (tonnes/day) | 0.0 | 0.0 | 0.0 | 0.0 | 3990.0 | 0.0 | 0.0 | 0.0 |
| Mass Flow | 825.6 | 201.4 | 625.6 | 200.0 | 7980.8 | 707.0 | 120.0 | 81.4 |
| Temperature (° C.) | 90 | 90 | 161 | 99 | 242 | 98 | 97 | 100 |

| Stream # | 1 | 6 | 8 | 15 | 4 | 7 | 9 |
|---|---|---|---|---|---|---|---|
| Component Mass Flow | | | | | | | |
| Water (tonnes/day) | 14365.0 | 70.0 | 14295.0 | 0.0 | 0.0 | 0.0 | 14295.0 |
| Furfural (tonnes/day) | 631.0 | 567.9 | 63.1 | 0.1 | 0.7 | 56.9 | 6.3 |
| Acetic Acid (tonnes/day) | 240.0 | 13.0 | 227.0 | 0.0 | 0.0 | 0.0 | 227.0 |
| SBP (tonnes/day) | 3591.0 | 3591.0 | 0.0 | 399.0 | 3591.0 | 399.0 | 0.0 |
| 1-MNP (tonnes/day) | 3591.0 | 3591.0 | 0.0 | 399.0 | 3591.0 | 399.0 | 0.0 |
| Mass Flow | 22418.0 | 7832.9 | 14585.1 | 798.1 | 7182.7 | 854.9 | 14528.3 |
| Temperature (° C.) | 90 | 90 | 90 | 242 | 242 | 94 | 94 |

TABLE 2

Distillation Column Summary

| | Units | D1 | D2 | D3 |
|---|---|---|---|---|
| Pressure | MPa | 0.1 | 0.1 | 0.1 |
| Reflux Ratio | | 0.5 | 1 | 1 |
| Distillate Rate | tonne/day | 707 | 120 | 200 |
| Number of trays | | 25 | 25 | 25 |
| Feed rate | tonne/day | 7833 | 201 | 826 |
| Reboiler Temperature | C | 242 | 100 | 161 |
| Reboiler Duty | MW | 41 | 5 | 6 |
| Steam usage (4.48 MPa) | tonne/day | 2106 | 262 | 326 |

TABLE 3

Liquid-Liquid Separator Summary

| | Units | LL1 | LL2 | LL3 |
|---|---|---|---|---|
| Pressure | MPa | 0.1 | 0.1 | 0.1 |
| Temperature | C | 90 | 90 | 95 |
| Feed rate | tonne/day | 22418 | 1027 | 15383 |

TABLE 4

Separation Scheme Results Summary

| | Units | |
|---|---|---|
| Furfural Recovery Rate | tonne/day | 624.0 |
| Furfural Recovery | | 98.9% |
| Furfural Purity | | 99.8% |
| Total energy requirement | MW | 52 |
| Steam Usage (650 psig) | tonne/day | 2694 |
| Steam Consumption | t/t FUR produced | 4.3 |

That which is claimed is:

1. A process for the extraction of furfural from a composition comprising furfural, water, at least one organic acid and a solvent mixture comprising an aromatic solvent and an oxygenate solvent wherein each of the solvents in the solvent mixture has a boiling point higher than of furfural, said process comprising:
   (a) subjecting the composition to a first liquid-liquid separation step to provide a first organic phase comprising the solvent mixture, a portion of the furfural and a portion of the at least one organic acid, and a first aqueous phase comprising the remainder of the furfural, and the remainder of the at least one organic acid;
   (b) subjecting the first organic phase to a first distillation step to provide a first top stream comprising furfural and a portion of the at least one organic acid, and a first bottom stream comprising the solvent mixture;
   (c) subjecting the first top stream from step (b) to a second liquid-liquid separation step to provide a second top stream enriched with furfural and a portion of the at least one organic acid, and a second bottom stream comprising the remainder of the furfural and a portion of the at least one organic acid; and
   (d) subjecting the second top stream from step (c) to a second distillation step to provide a third top stream comprising a furfural-water azeotrope and a portion of the at least one organic acid, and a third bottom stream comprising furfural.

2. The process according to claim 1, wherein the composition is derived from a product stream of a pentose dehydration step wherein a pentose feed stream is dehydrated.

3. The process according to claim 2, wherein the pentose feed stream is derived from the hydrolysis of a lignocellulosic biomass.

4. The process according to claim 1, wherein the aromatic solvent is selected from the group consisting of 1-ethyl-2,3-dimethylbenzene, 1-ethyl-2,5-dimethylbenzene, 1-ethyl-2,4-dimethylbenzene, 1-ethyl-3,4-dimethylbenzene, 1,2,3,5-tetramethylbenzene, 1,2,3,4-tetramethylbenzene, 1,2,4,5-tetramethylbenzene, naphthalene, 1-methylnaphthalene, 2-methylnaphthalene, n- and sec-propyl-methyl benzenes (with the methyl group located in 2-, 3-, 4- or 5-position) n- and sec-butyl benzene, n- and sec-pentyl benzene, or any combination thereof.

5. The process according to claim 1, wherein the oxygenate solvent is selected from the group consisting of: propyl guaiacol; propyl syringol; guaiacyl propanol, syringyl propanol; nonyl phenol; o-, m-, p-substituted cresols; guaiacol; 2-methoxy-4-propylphenol; eugenol; 2,6-xylenol; sec-butyl phenol and 2,5-xylenol; and any combination thereof.

6. The process according to claim 1, wherein the solvent mixture comprises a phenolic to aromatic volume ratio of in the range of from 20:80 to 80:20.

7. The process according to claim 1, wherein the solvent mixture comprises a phenolic to aromatic volume ratio of 30:70.

8. The process according to claim 1, wherein the second bottom stream of step (c) is subjected to a third distillation step to provide a fourth top stream comprising a furfural-water azeotrope, and a fourth bottom stream comprising water and a portion of the at least one organic acid.

9. The process according to claim 1, wherein the first aqueous phase of step (a) and a portion of the first bottom stream of step (b) are conveyed to a third liquid-liquid separator and subjected to a third liquid-liquid separation step to provide a fifth top stream comprising furfural and the solvent mixture, and an aqueous waste stream comprising water and at least one organic acid.

10. The process according to claim 1, wherein the fifth top stream is recycled to the first distillation step.

* * * * *